(12) United States Patent
Harris et al.

(10) Patent No.: US 7,884,045 B2
(45) Date of Patent: *Feb. 8, 2011

(54) REGENERATION OF IONIC LIQUID CATALYST AND RECOVERY OF AN OIL

(75) Inventors: Thomas V. Harris, Benicia, CA (US); Saleh Elomari, Fairfield, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/705,943

(22) Filed: Feb. 15, 2010

(65) Prior Publication Data

US 2010/0234208 A1 Sep. 16, 2010

Related U.S. Application Data

(63) Continuation of application No. 11/316,450, filed on Dec. 20, 2005, now Pat. No. 7,691,771.

(51) Int. Cl.
| | |
|---|---|
| B01J 20/34 | (2006.01) |
| B01J 23/90 | (2006.01) |
| B01J 21/20 | (2006.01) |
| B01J 25/04 | (2006.01) |
| B01J 27/28 | (2006.01) |
| B01J 29/90 | (2006.01) |
| B01J 31/40 | (2006.01) |
| B01J 38/00 | (2006.01) |
| B01J 38/58 | (2006.01) |
| B01J 38/04 | (2006.01) |
| B01J 38/10 | (2006.01) |
| B01J 31/00 | (2006.01) |

(52) U.S. Cl. .................... 502/150; 502/20; 502/22; 502/30; 502/34; 502/53

(58) Field of Classification Search ................ 502/150, 502/20, 22, 30, 34, 53
See application file for complete search history.

(56) References Cited

U.S. PATENT DOCUMENTS

| | | | |
|---|---|---|---|
| 4,122,245 A | 10/1978 | Nardi et al. | |
| 4,463,071 A | 7/1984 | Gifford et al. | |
| 4,463,072 A | 7/1984 | Gifford et al. | |
| 5,104,840 A | 4/1992 | Chauvin et al. | |
| 5,391,527 A | 2/1995 | Kojima et al. | |
| 5,731,101 A | 3/1998 | Sherif et al. | |
| 6,096,680 A | 8/2000 | Park | |
| 6,797,853 B2 | 9/2004 | Houzvicka et al. | |
| 7,651,970 B2 * | 1/2010 | Elomari et al. | 502/150 |
| 7,678,727 B2 * | 3/2010 | Harris et al. | 502/150 |
| 2004/0077914 A1 | 4/2004 | Zavilla et al. | |
| 2004/0133056 A1 | 7/2004 | Liu et al. | |

OTHER PUBLICATIONS

Christopher, J. Adams, et al., Stereoselective hydrogenation reactions in chloroaluminate (III) ionic liquids: a new method for the reduction of aromatic compounds, Institute of Applied Catalysis, School of Chemistry, 1999, 1043-1044, Received in Cambridge, UK, Feb. 15, 1999, Accepted Apr. 19, 1999.

Adams, et al., Friedel-Craft reactions in room temperature ionic liquids, Chem Commun, 1998, pp. 2097-2098.

* cited by examiner

Primary Examiner—James E McDonough
(74) Attorney, Agent, or Firm—Susan M. Abernathy; Steven H. Roth

(57) ABSTRACT

A process for regenerating a used acidic ionic liquid catalyst, comprising: a. contacting the catalyst and hydrogen with a supported hydrogenation catalyst under hydrogenation conditions; and b. recovering a conjunct polymer that is a clear and colorless oil from the catalyst. A process for regenerating a used acidic ionic liquid catalyst which has been deactivated by conjunct polymers comprising the steps of contacting the used catalyst and hydrogen with a supported hydrogenation catalyst in a reaction zone under hydrogenation conditions in the presence of an inert hydrocarbon in which saturated conjunct polymers are soluble for a time sufficient to hydrogenate at least a portion of the conjunct polymers; and recovering the saturated conjunct polymers. Also, a process comprising: contacting the used acidic ionic liquid catalyst and hydrogen with a hydrogenation catalyst comprising a hydrogenation component under hydrogenation conditions; and recovering a conjunct polymer that is a clear and colorless oil.

20 Claims, 1 Drawing Sheet

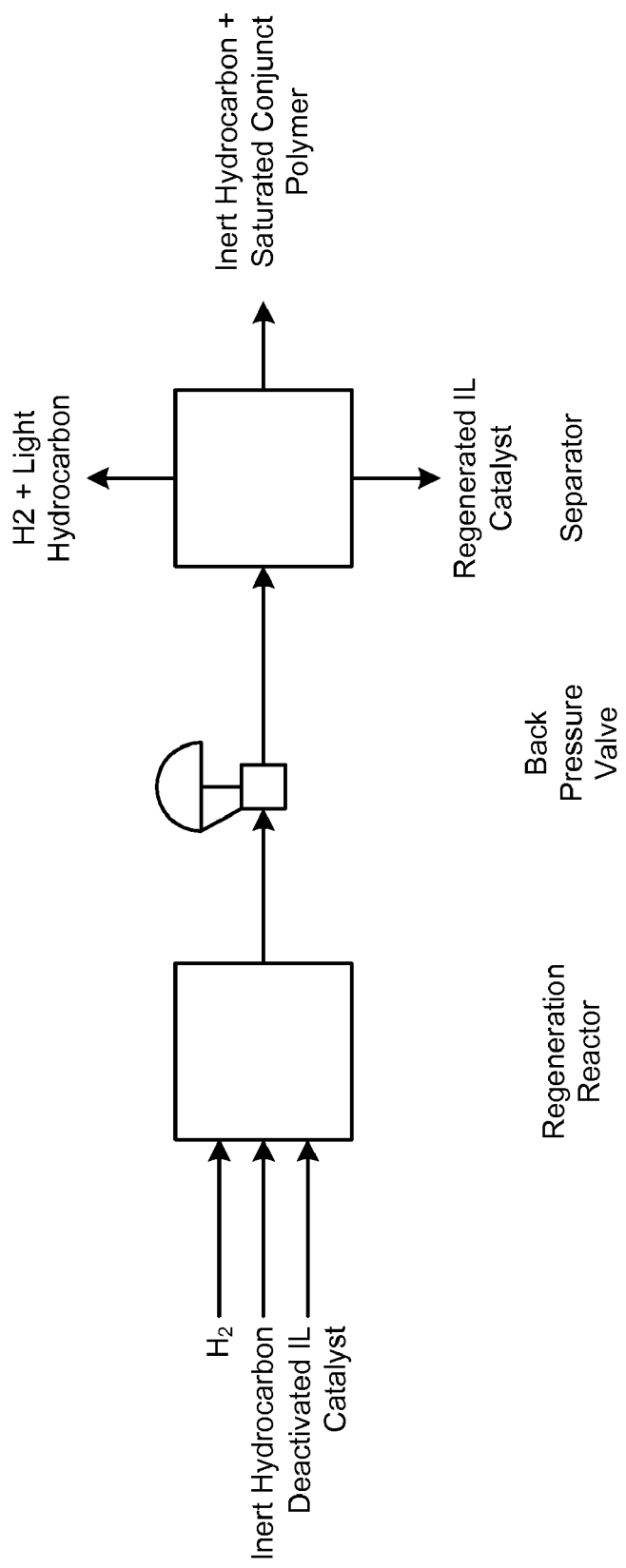

REGENERATION OF IONIC LIQUID CATALYST AND RECOVERY OF AN OIL

This application is a continuation of U.S. patent application Ser. No. 11/316,450, published as US 2007-0142215 A1, filed on Dec. 20, 2005, and fully incorporated herein.

FIELD OF THE INVENTION

The present invention relates to methods for the regeneration of ionic liquid catalysts and the recovery of an oil.

BACKGROUND OF THE INVENTION

Ionic liquids are liquids that are composed entirely of ions. The so-called "low temperature" Ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization acetylation, metatheses, and copolymerization reactions.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but not limited to, $BE_4^-$, $PF_6^-$, haloaluminates such as $Al_2Cl_7^-$ and $Al_2Br_7^-$, $[(CF_3SO_2)_2N)]^-$, alkyl sulphates ($RSO_3^-$), carboxylates ($RCO_2^-$) and many other. The most catalytically interesting ionic liquids are those derived from ammonium halides and Lewis acids (such as $AlCl_3$, $TiCl_4$, $SnCl_4$, $FeCl_3$ . . . etc). Chloroaluminate ionic liquids are perhaps the most commonly used ionic liquid catalyst systems.

Examples of such low temperature ionic liquids or molten fused salts are the chloroaluminate salts. Alkyl imidazolium or pyridinium salts, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245. Other patents which discuss the use of fused salts from aluminum trichloride and alkylimidazolium halides as electrolytes are U.S. Pat. Nos. 4,463,071 and 4,463,072.

U.S. Pat. No. 5,104,840 describes ionic liquids which comprise at least one alkylaluminum dihalide and at least one quaternary ammonium halide and/or at least one quaternary ammonium phosphonium halide; and their uses as solvents in catalytic reactions.

U.S. Pat. No. 6,096,680 describes liquid clathrate compositions useful as reusable aluminum catalysts in Friedel-Crafts reactions. In one embodiment, the liquid clathrate composition is formed from constituents comprising (i) at least one aluminum trihalide, (ii) at least one salt selected from alkali metal halide, alkaline earth metal halide, alkali metal pseudohalide, quaternary ammonium salt, quaternary phosphonium salt, or ternary sulfonium salt, or a mixture of any two or more of the foregoing, and (iii) at least one aromatic hydrocarbon compound.

Aluminum-containing catalysts are among the most common Lewis acid catalysts employed in Friedel-Craft reactions. Friedel-Craft reactions are reactions which fall within the broader category of electrophylic substitution reactions including alkylations.

Other examples of ionic liquids and their methods of preparation may also be found in U.S. Pat. Nos. 5,731,101; 6,797,853 and in U.S. Patent Application Publications 2004/0077914 and 2004/0133056.

Hydrogenation in chloroaluminate ionic liquids in the presence of an electropositive metal and HCl was reported by K. R. Seddon et al in *Chem. Commun.*, 1999, 1043-1044.

As a result of use, ionic liquid catalysts become deactivated, i.e. lose activity, and may eventually need to be replaced. However, ionic liquid catalysts are expensive and replacement adds significantly to operating expenses by in some cases requiring shut down of an industrial process. One of the heretofore unsolved problems impeding the commercial use of chloroaluminate ionic liquid catalysts has been the inability to regenerate and recycle them. The present invention provides methods to regenerate acidic chloroaluminate ionic liquid catalysts overcoming this obstacle and paving the way for the practical, commercial use of these environmentally friendly catalysts.

SUMMARY OF THE INVENTION

Among other things, the present invention provides a process for regenerating a used acidic ionic liquid catalyst comprising contacting the used ionic liquid catalyst and hydrogen with a supported hydrogenation catalyst comprising a hydrogenation component on a support in a reaction zone under hydrogenation conditions for a time sufficient to increase the activity of the used catalyst.

BRIEF DESCRIPTION OF THE FIGURE

The FIGURE is a block diagram of an embodiment of an ionic liquid catalyst regeneration using supported hydrogenation catalysts according to the invention.

DETAILED DESCRIPTION

The present invention relates to a process for the regeneration of spent or deactivated acidic ionic liquid-based catalysts i.e. those catalysts which have lost all or some of their catalytic activity. The present process is being described and exemplified with reference certain specific ionic liquid catalysts and processes catalyzed thereby, but such description is not intended to limit the scope of the invention. The methods described may be applied to other catalysts and processes by those persons having ordinary skill based on the teachings, descriptions and examples included herein.

The specific examples used herein refer to alkylation processes using ionic liquid systems, which are amine-based cationic species mixed with aluminum chloride. In such systems, to obtain the appropriate acidity suitable for the alkylation chemistry, the ionic liquid catalyst is generally prepared to full acidity strength by mixing one molar part of the appropriate ammonium chloride with two molar parts of aluminum chloride. The catalyst exemplified for the alkylation process is a 1-alkyl-pyridinium chloroaluminate, such as 1-butyl-pyridinium heptachloroaluminate.

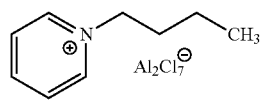

1-Butyl-pyridinium heptachloroaluminate

In general, a strongly acidic ionic liquid is necessary for paraffin alkylation, e.g. isoparaffin alkylation. In that case, aluminum chloride, which is a strong Lewis acid, in a combination with a small concentration of a Broensted acid, is a preferred catalyst component in the ionic liquid catalyst scheme.

While not being bound to this or any other theory of operation, the present invention is based in part on our discovery that one of the major catalyst deactivation mechanisms is the formation of by-products known as conjunct polymers. The term conjunct polymer was first used by Pines and Ipatieff to distinguish these polymeric molecules from the usual polymers. Unlike typical polymers, conjunct polymers are polyunsaturated cyclic, polycyclic and acyclic molecules formed by concurrent acid-catalyzed reactions including, among others, polymerization, alkylation, cyclization, and hydride transfer reactions. Conjunct polymers consist of unsaturated intricate network of molecules that may include one or a combination of 4-, 5-, 6- and 7-membered rings in their skeletons. Some examples of the likely polymeric species were reported by Miron et al. (*Journal of chemical and Engineering Data,* 1963) and Pines (*Chem. Tech,* 1982). These molecules contain double and conjugated double bonds in intricate structures containing a combination of cyclic and acyclic skeletons.

The conjunct polymers deactivate the chloroaluminate ionic liquid catalysts by weakening the acid strength of the catalyst through the formation of complexes of conjunct polymers and $AlCl_3$ possibly by means of electron-donor/electron-acceptor interactions. The conjunct polymers with their double bonds are the donors and the Lewis acid ($AlCl_3$) is the acceptor. Using their double bonds, the conjunct polymers coordinate to the Lewis acid ($AlCl_3$) in the ionic liquid and rendering the butylpyridinium chloroaluminate catalyst less active. Thus, the acidity of the catalyst becomes weaker and the overall catalytic activity becomes compromised and no longer effective for the intended purpose. Thus, the catalyst performance will become a function of the concentration of conjunct polymers in the ionic liquid phase. As more conjunct polymers accumulate in the ionic liquid phase the catalyst becomes less active. So, removal of all or a suitable portion of the conjunct polymers from the ionic liquid phase is a significant aspect of the present process for ionic liquids catalyst regeneration.

The term "conjunct polymer" as used herein also includes any other species which might complex to $AlCl_3$ by pi bonding or sigma bonding or other means, which results in those species binding to the ionic liquid, so they are not removable by simple hydrocarbon extraction.

It is believed that deactivation of the catalyst by the presence of conjunct polymers is, in part at least, caused by coordination and complex formation between the Lewis acid $AlCl_3$ (electron pair acceptor) and the conjunct polymers (electron donors). In such complexes, the $AlCl_3$ is no longer available for catalysis since it is tied-up in the $AlCl_3$-conjunct polymers complexes. It also appears that the presence (or accumulation) of conjunct polymer molecules in the catalyst phase is not by virtue of being miscible in the ionic liquid phase. While conjunct polymers may be somewhat miscible in the ionic liquids, their accumulation in the catalyst phase is more likely to being bound by strong acid-base interactions (complexation) rather than being soluble in the ionic liquid phase.

Conjunct polymers isolated from the catalyst phase by means of hydrolysis are highly soluble in hydrocarbons. However, attempts to remove them from the catalyst phase prior to hydrolysis by simple extraction methods with hydrocarbon solvents such as hexane, decane and toluene were unsuccessful. Other more polar solvents such as $CH_2Cl_2$ and chloroform may dissolve a chloroaluminate ionic liquid and therefore are not selective solvents for dissolving and removing the conjunct polymers. Conjunct polymers may be isolated by hydrolysis. However, these methods of isolating the conjunct polymers are destructive, and result in an actual loss of a catalytic component ($AlCl_3$). The hydrolysis methods hydrolyze the catalytic component ($AlCl_3$) and transform it into inactive aluminum hydroxide and aluminum oxide. This indicates that the conjunct polymers are tightly held in the ionic liquid phase by fairly strong type of bonding system. Therefore, any successful attempt to reactivate and regenerate the catalyst must involve the removal of conjunct polymers to release aluminum trichloride from the $AlCl_3$-conjunct polymer complexes without destroying, consuming, or irreversibly tying up the $AlCl_3$. In other words, one objective is to free the catalyst by replacing the conjunct polymers with other basic species that simply displace the polymer without destroying the catalyst or by suppressing the ability of conjunct polymers to form complexes with Lewis acids (aluminum chloride).

The deactivated catalyst can be revived in a nondestructive manner by freeing up the $AlCl_3$ from conjunct polymer-$AlCl_3$ complex. In principle, this can be accomplished by saturation of the double bonds of the conjunct polymers to eliminate their ability to coordinate to the Lewis acid ($AlCl_3$). By hydrogenation, the double bonds of the conjunct polymers will be saturated and no longer be able to be coordinated or complexed to $AlCl_3$. $AlCl_3$ no longer bound by conjunct polymers is then released to take part in catalytic reactions.

Among other things the present invention provides a process for the removal of the conjunct polymers from a used ionic liquid catalyst by saturating the double bonds of the conjunct polymers by means of hydrogenation using a supported hydrogenation catalyst thereby increasing the activity of the ionic liquid catalyst.

Hydrogenation is a well-established process both in the chemical and petroleum refining industries. Hydrogenation is conventionally carried out in the presence of a catalyst which usually comprises a metal hydrogenation component on a porous support material, such as a natural clay or a synthetic oxide. Nickel is often used as a hydrogenation component, as are noble metals such as platinum, palladium, rhodium and iridium. Typical support materials include kieselguhr, alumina, silica and silica-alumina. Depending upon the ease with which the feed may be hydrogenated, the hydrogen pressures used may vary from quite low to very high values, typically from about 100 to 2,500 psig.

The hydrogenation catalyst used in this invention may be any one of metallic or non-metallic catalysts which have hydrogenating ability. The preferred catalyst comprises at least one hydrogenation component selected from Group VI-B and VIII, present as metals, oxides, or sulfides. Specific examples of the metallic catalysts are Fe, Co, Ni, Ru, Rh, Pd, Ir, Os, Pt, Cr, Mn, Ti, V, Zr, Mo, and W. Specific examples of the non-metallic catalysts are Te and As. These metals or non-metals may be used singly or in combination.

Noble metals such as palladium, platinum, or ruthenium, applied to diverse supports such as silicon dioxide, aluminum oxide, graphite, or activated charcoal, are well suited for the hydrogenation of organic and inorganic compounds. The hydrogenation component may also be supported on a refractory inorganic base, for example, alumina, silica, and composites of alumina-silica, alumina-boria, silica-alumina-magnesia, and silica-alumina-titania and materials obtained by adding zeolites and other complex oxides thereto. The refractory inorganic oxide is a material that has adequate mechanical strength and chemical stability at the reaction temperature of the catalyst.

The catalyst of the present invention can be manufactured by supporting catalytically active components on a catalyst carrier. The active components may be deposited on the surface of the catalyst carrier after the carrier has been formed, or they may be incorporated into the catalyst by being added to the carrier material during the formation of the catalyst carrier. Many such methods of preparation are known.

As noted previously, ionic liquid catalysts may become deactivated during use. For example, in an alkylate production unit, light ($C_2$-$C_5$) olefins and isoparaffin feeds are contacted in the presence of a catalyst that promotes the alkylation reaction. In one embodiment of a process in accordance with the present invention, this catalyst is a chloroaluminate ionic liquid. The reactor, which may be a stirred tank or other type of contactor (e.g., riser reactor), produces a biphasic mixture of alkylate hydrocarbons, unreacted isoparaffins, and ionic liquid catalyst containing some conjunct polymers. The dense catalyst/conjunct polymer phase may be separated from the hydrocarbons by gravity settling in a decanter. This catalyst will be partially deactivated by the conjunct polymers binding to $AlCl_3$. The recovered catalyst can be reactivated in a reaction system hydrogenation with a supported hydrogenation catalyst. The products of this step will be reactivated catalyst and hydrogenated conjunct polymers among others as described herein. The reactivated catalyst and the hydrogenated conjunct polymers can be separated, for example, by solvent washing, decantation, and filtration.

It is not necessary to regenerate the entire charge of catalyst. In some instances only a portion or slipstream of the catalyst charge is regenerated. In those instances only as much ionic liquid catalyst is regenerated as is necessary to maintain a desired level of catalyst activity in the process in which the ionic liquid is used as the catalyst.

In one embodiment of the present invention with reference to the FIGURE, a used ionic liquid catalyst/conjunct polymer mixture is introduced continuously into a regeneration reactor, which contains a fixed bed of a supported hydrogenation catalyst. Hydrogen gas and inert hydrocarbons in which hydrogenated conjunct polymers are soluble are fed into the reactor at the desired rate. The solvent may be a normal hydrocarbon ranging from $C_5$-$C_{15}$, preferably $C_5$-$C_8$. The residence time, temperature and pressure of the reactor will be selected to allow adequate hydrogenation of the conjunct polymers. The reaction product is withdrawn and sent to a separator. This mixture is then separated into three streams, one comprising hydrogen and light hydrocarbons, a second comprising inert hydrocarbons and saturated conjunct polymer and a third comprising regenerated ionic liquid catalyst. The denser and more viscous regenerated catalyst phase settles to the bottom and can be recovered by means of a gravity decanter. The reactivated ionic liquid catalyst is returned to the alkylation reactor. The solvent/conjunct polymer mix is separated by distillation to recover the solvent. The block diagram in the FIGURE is not meant to restrict the present invention any sort or type of reactor. Also, the FIGURE shows an inert hydrocarbon entering the reactor together with hydrogen and the deactivated ionic liquid. That is an optional implementation. The hydrocarbon could be left out entirely or it could be added to the separator to allow extraction and separation simultaneously. Other modifications are possible and are included in the scope of the present invention.

Hydrogenation conditions will generally include temperatures of –20° C.-200° C., preferably 50° C.-150° C., pressures of atmospheric-5000 psig, preferably 50-500 psig, and a contact time of 0.1 minute-24 hours, and preferably from ½-2 hours in a normal hydrocarbon as a solvent.

The following Examples are illustrative of the present invention, but are not intended to limit the invention in any way beyond what is contained in the claims which follow.

EXAMPLES

Example 1

Preparation of Fresh 1-Butylpyridinium Chloroaluminate Ionic Liquid Catalyst A (Fresh IL A)

1-butyl-pyridinium chloroaluminate is a room temperature ionic liquid prepared by mixing neat 1-butyl-pyridinium chloride (a solid) with neat solid aluminum trichloride in an inert atmosphere. The syntheses of butylpyridinium chloride and the corresponding 1-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The neat mixture was sealed and let to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, unreacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shiny solid. $^1$H-NMR and $^{13}$C-NMR were consistent with the desired 1-butyl-pyridinium chloride and no impurities were observed.

1-butylpyridinium chloroaluminate was prepared by slowly mixing dried 1-butylpyridinium chloride and anhydrous aluminum chloride ($AlCl_3$) according to the following procedure. The 1-butylpyridinium chloride (prepared as described above) was dried under vacuum at 80° C. for 48 hours to get rid of residual water (1-butylpyridinium chloride is hydroscopic and readily absorbs water from exposure to air). Five hundred grams (2.91 mol.) of the dried 1-butylpyridinium chloride were transferred to a 2-Liter beaker in a nitrogen atmosphere in a glove box. Then, 777.4 gm (5.83 mol.) of anhydrous powdered $AlCl_3$ (99.99% from Aldrich) were added in small portions (while stirring) to control the temperature of the highly exothermic reaction. Once all the $AlCl_3$ was added, the resulting amber-looking liquid was left to gently stir overnight in the glove box. The liquid was then filtered to remove any un-dissolved $AlCl_3$. The resulting acidic 1-butyl-pyridinium chloroaluminate was used as the catalyst for the alkylation of isopentane with ethylene.

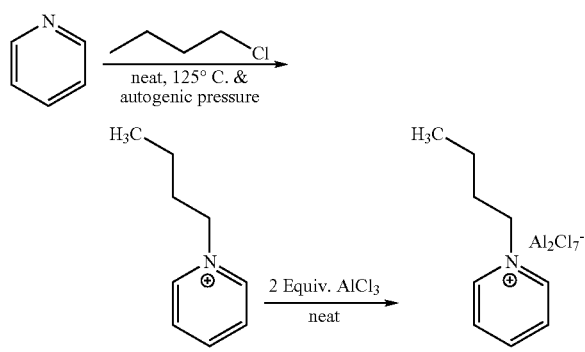

Example 2

Preparation of "Deactivated" 1-Butylpyridinium Chloroaluminate Ionic Liquid Catalyst (Deactivated Catalyst A)

"Deactivated" or "used" 1-butylpyridinium chloroaluminate ionic liquid catalyst was prepared from "fresh" 1-butylpyridinium chloroaluminate ionic liquid catalyst by carrying out the isobutane alkylation reaction in a continuous flow microunit under catalyst recycle with accelerated fouling conditions.

The microunit consists of feed pumps for isobutane and butenes, a stirred autoclave reactor, a back pressure regulator, a three phase separator, and a third pump to recycle the separated ionic liquid catalyst back to the reactor. The reactor was operated at 80 to 100 psig pressure and with cooling to maintain a reaction temperature of ~10° C. To start the reaction, isobutane, butenes, and HCl were pumped into the autoclave at the desired molar ratio (isobutane/butenes>1.0), through the back pressure regulator, and into the three phase separator. At the same time, fresh chloroaluminate ionic liquid catalyst was pumped into the reactor at a rate pre-calculated to give the desired catalyst/feed ratio on a volumetric basis. As the reaction proceeded, ionic liquid separated from the reactor effluent and collected in the bottom of the three phase separator. When a sufficient level of catalyst built up in the bottom of the separator, the flow of fresh ionic liquid was stopped and catalyst recycle from the bottom of the separator was started. In this way, the initial catalyst charge was continually used and recycled in the process.

The following process conditions were used to generate Deactivated Catalyst A (1-butylpyridinium chloroaluminate ionic liquid catalyst) from Fresh Catalyst A:

| Process Variable | |
| --- | --- |
| Isobutane pump rate | 4.6 g/min |
| Butene pump rate | 2.2 g/min |
| IL Catalyst pump rate | 1.6 g/min |
| HCl flow rate | 3.0 SCCM |
| pressure | 100 psig |
| temperature | 10° C. |

The reaction was continued for 72 hours when it was judged that the catalyst had become sufficiently deactivated.

Example 3

Determination of the Amounts of Conjunct Polymer and Olefin Oligomers in Deactivated IL A The wt % of conjunct polymers in the spent (deactivated) ionic liquid was determined by hydrolysis of known weights of the spent catalyst. The example below is a typical procedure for measuring conjunct polymers in a given spent catalyst. In a glove box, 15 gm of a spent ionic liquid catalyst in a flask were rinsed first with 30-50 ml of anhydrous hexane to remove (from the spent catalyst) any residual hydrocarbon or olefinic oligomers. The hexane rinse was concentrated under reduced pressure to give only 0.02 gm of yellow oil (0.13%). Then, 50 ml of anhydrous hexane was added to the rinsed catalyst followed by slow addition of 15 ml of water, and the mixture was stirred at 0° C. for 15-20 minutes. The resulting mixture was diluted with additional 30 ml hexanes and stirred well for additional 5-10 minutes. The mixture was allowed to settle down to two layers solution and some solid residue. The organic layer was recovered by decanting. The aqueous layer was further washed with additional 50 ml hexanes. The hexanes layers were combined and dried over anhydrous $MgSO_4$, filtered and concentrated to give 2.5 gm (16.7 wt % of the spent catalyst) of viscous dark orange-reddish oil. It was determined therefore that this particular spent catalyst contains 0.13% oligomers and 16.7% conjunct polymers. The hydrolysis can also be accomplished using acidic (aqueous HCl) or basic (aqueous NaOH) solutions.

Example 4

Characterization of Recovered Conjunct Polymer from Deactivated IL A

The recovered conjunct polymers according to the procedure described in Example 3 were characterized by elemental analysis and by infrared, NMR, GC-Mass and UV and spectroscopy methods. The recovered conjunct polymers have hydrogen/carbon ratio of 1.76 and chlorine content of 0.8%. $^1$H-NMR and $^{13}$C-NMR showed the presence of olefinic protons and olefinic carbons. Infrared spectroscopy indicated the presence of olefinic regions and the presence of cyclic systems and substituted double bonds. GCMS showed the conjunct polymers to have molecular weights ranging from 150-mid 600s. The recovered conjunct polymers have boiling ranges of 350-1100° F. as indicated by high boiling simulated distillation analysis. UV spectroscopy showed a UV $\lambda_{max}$ at 250 nm pointing highly conjugated double bonds systems.

Example 5

Removal of Conjunct Polymers from Deactivated Catalyst A by Hydrogenation with Palladium on Carbon Catalyst In a drybox, 3.0 grams of 10% palladium on carbon (Pd/C) catalyst was charged to a 100 mL stirred autoclave. Next, ~30 mL (31.33 g) of Deactivated Catalyst A was added. The autoclave was taken out of the drybox and charged with 900 psig hydrogen at ambient temperature. The reactor was heated to 100° C. for 14.75 hours and then cooled. A portion of the recovered catalyst (22.48 g) was extracted three times with 7 g of dry hexane. The hexane extracts were combined and evaporated under a stream of nitrogen to yield 0.408 g of clear, colorless oil. This corresponds to a recovery of 9.9 wt % of the conjunct polymer originally present in the Deactivated Catalyst A.

An 11.26 g sample of hexane-extracted, hydrogenated Deactivated Catalyst A was weighed into a bottle and hydrolyzed as described in Example 3. After combining the hexane extracts and evaporation under a stream of nitrogen, 0.87 g of a non-volatile residue was recovered. This corresponds to 7.73 wt % conjunct polymer remaining on the Deactivated Catalyst A after hydrogenation with 10% Pd/C catalyst. This corresponds to removal of 37.2 wt % of the conjunct polymer originally present in Deactivated Catalyst A. The difference between 9.9% hydrogenated conjunct polymer recovered and 37.2% conjunct polymer removed from Deactivated Catalyst A is due to losses during hexane evaporation of light components formed by hydrocracking.

Example 6

Removal of Conjunct Polymer from Deactivated Catalyst B by Hydrogenation with Palladium on Carbon Catalyst The procedure of Example 5 was repeated using Deactivated Catalyst B (31.33 g). The amount of 10% Pd/C catalyst was 0.10 g. Hexane, 30 mL, was also added to aid stirring. The initial pressure at ambient temperature was 900 psig. After heating 18 hours at 100° C. and cooling, the pressure was 650 psig. After extraction of hexane and evaporation of light components, 0.43 g of clear, colorless, oil was recovered. This corresponds to a recovery (as hydrogenated conjunct polymer) of 5.92 wt % of the original conjunct polymer present in Deactivated Catalyst B.

A sample of 15.009 g of Deactivated Catalyst B after hydrogenation and hexane extraction was placed in a bottle and hydrolyzed as described in Example 3. After hexane extraction and evaporation of the volatiles from the combined hexane extracts, a residue of 1.56 g of conjunct polymer was obtained. This corresponds to a conjunct polymer content after hydrogenation of 10.4 wt %. Alternatively, 61.6 wt % of the conjunct polymer originally present in Deactivated Catalyst B was removed by hydrogenation.

Example 7

Removal of Conjunct Polymer from Deactivated Catalyst C by Hydrogenation with Palladium on Alumina Catalyst The procedure of Example 5 was repeated using Deactivated Catalyst C (21.278 g). The hydrogenation catalyst was 1.04 g of 1.0 wt % Pd on $Al_2O_3$. In this experiment, no hexane was added to aid stirring. The initial pressure at 100° C. was ~1212 psig and after heating 4.5 hours at 100° C., the pressure was ~1090 psig. After extraction of hexane and evaporation of light components, no oil was recovered.

A sample of 17.33 g of Deactivated Catalyst C after hydrogenation and hexane extraction was placed in a bottle and hydrolyzed as described in Example 3. After hexane extraction and evaporation of the volatiles from the combined hexane extracts, a residue of 1.49 g of conjunct polymer was obtained. This corresponds to conjunct polymer content after hydrogenation of 8.60 wt %. Alternatively, 37.4 wt % of the conjunct polymer originally present in Deactivated Catalyst C was removed by hydrogenation.

Example 8

Removal of Conjunct Polymer from Deactivated Catalyst C by Hydrogenation with Supported Palladium on Alumina Catalyst The procedure of Example 5 was repeated using Deactivated Catalyst C (24.88 g). The hydrogenation catalyst was 1.15 g of 0.5 wt % Pd on $Al_2O_3$. In this experiment, no hexane was added to aid stirring. The initial pressure at 100° C. was ~1312 psig and after heating 4.5 hours at 100° C., the pressure was ~1200 psig. After extraction of hexane and evaporation of light components, no oil was recovered.

A sample of 20.52 g of Deactivated Catalyst C after hydrogenation and hexane extraction was placed in a bottle and hydrolyzed as described in Example 3. After hexane extraction and evaporation of the volatiles from the combined hexane extracts, a residue of 2.09 g of conjunct polymer was obtained. This corresponds to a conjunct polymer content after hydrogenation of 10.18 wt %. Alternatively, 26.0 wt % of the conjunct polymer originally present in Deactivated Catalyst C was removed by hydrogenation.

Example 9

Removal of Conjunct Polymer from Deactivated Catalyst C by Hydrogenation with Supported Platinum on Alumina Catalyst The procedure of Example 5 was repeated using Deactivated Catalyst C (20.78 g). The hydrogenation catalyst was 1.46 g of 0.5 wt % Pt on $Al_2O_3$. In this experiment, no hexane was added to aid stirring. The initial pressure at 100° C. was ~1250 psig and after heating 4.5 hours at 100° C., the pressure was ~1190 psig. After extraction of hexane and evaporation of light components, no oil was recovered.

A sample of 17.55 g of Deactivated Catalyst C after hydrogenation and hexane extraction was placed in a bottle and hydrolyzed as described in Example 3. After hexane extraction and evaporation of the volatiles from the combined hexane extracts, a residue of 2.18 g of conjunct polymer was obtained. This corresponds to a conjunct polymer content after hydrogenation of 12.4 wt %. Alternatively, 9.7 wt % of the conjunct polymer originally present in Deactivated Catalyst C was removed by hydrogenation.

Example 10

Removal of Conjunct Polymer from Deactivated Catalyst C by Hydrogenation with Supported Ni Catalyst The procedure of Example 5 was repeated using Deactivated Catalyst C (19.20 g). The hydrogenation catalyst was 1.02 g of Ni on synthetic mica montmorillonite. The hydrogenation catalyst had been previously reduced in flowing hydrogen at ambient pressure and at 450° C. In this experiment, no hexane was added to aid stirring. The initial pressure at 100° C. was ~1250 psig and after heating 4 hours at 100° C., the pressure was ~1200 psig. After extraction of hexane and evaporation of light components, no oil was recovered.

A sample of 15.76 g of Deactivated Catalyst C after hydrogenation and hexane extraction was placed in a bottle and hydrolyzed as described in Example 3. After hexane extraction and evaporation of the volatiles from the combined hexane extracts, a residue of 1.82 g of conjunct polymer was obtained. This corresponds to conjunct polymer content after hydrogenation of 11.6 wt %. Alternatively, 16.0 wt % of the conjunct polymer originally present in Deactivated Catalyst C was removed by hydrogenation.

Example 11

Determination of the Activity of Regenerated Butylpyridinium Chloroaluminate Ionic Liquid Catalyst Butylpyridinium chloroaluminate ionic liquid catalyst was tested for activity by using it as the catalyst in the alkylation of isopentane with ethylene. Comparisons among fresh, spent and regenerated catalysts were made. The alkylation of isopentane with ethylene was done according to the following procedure. A 300 cc autoclave was charged with 20 gm of ionic liquid catalyst, 100 gm anhydrous isopentane, 10 gm ethylene and 0.3 gm anhydrous HCl. The reaction was then stirred ~1200 rpm and heated to 50° C. at autogenic pressures. The starting pressure was usually 280-320 psi. The reaction was usually complete when the pressure dropped down to single digits. In the case of slow going reaction, the reaction was allowed to go on for 1 hr. At the end of the reaction, the reactor was vented out and a gas sample was checked by GC for ethylene concentration. The liquid reaction mixture was allowed to settle into 2 phases. The organic phase was decanted and analyzed for product distribution by GC analysis. The following Table 1 draws a comparison among the freshly made, the spent and the regenerated catalysts.

TABLE 1

|  | Fresh Catalyst | Spent Catalyst | Regenerated Catalyst |
|---|---|---|---|
| Reaction Time | 6-9 min. | 60 min. | 4-7 min. |
| Starting Pressure | 300 psi | 286 psi | 350 psi |
| Ending pressure | 11 | 302 psi | 7 |
| iC5 wt % | 72 | 98 | 61 |
| C7s wt %: |  |  |  |
| 2,3-DM-Pentane | 8.23 | 0.9 | 8.5 |
| 2,4-DM-Pentane | 10 | 0.6 | 11.3 |
| Other C7s | 0.77 | 0.1 | 1.2 |
| 2,3DM/2,4DM | 0.82 | 1.5 | 0.75 |

There are numerous variations on the present invention which are possible in light of the teachings and supporting examples described herein. It is therefore understood that within the scope of the following claims, the invention may be practiced otherwise than as specifically described or exemplified herein.

What is claimed is:

1. A process for regenerating a used acidic ionic liquid catalyst, comprising:
    a. contacting the used acidic ionic liquid catalyst and hydrogen with a supported hydrogenation catalyst comprising a hydrogenation component under hydrogenation conditions; and
    b. recovering a conjunct polymer that is a clear and colorless oil from the used acidic ionic liquid catalyst.
2. The process of claim 1, wherein the hydrogenation component comprises palladium, platinum, or ruthenium.
3. The process of claim 2, wherein the hydrogenation component comprises palladium.
4. The process of claim 1, wherein the conjunct polymer is recovered by solvent extraction.
5. The process of claim 1, wherein the hydrogenation conditions include temperatures of −20° C. to 200° C.
6. The process of claim 1, wherein the supported hydrogenation catalyst is supported on carbon.
7. A process for regenerating a used acidic ionic liquid catalyst which has been deactivated by conjunct polymers comprising the steps of contacting the used ionic liquid catalyst and hydrogen with a supported hydrogenation catalyst comprising a hydrogenation component on a support in a reaction zone under hydrogenation conditions in the presence of an inert hydrocarbon in which saturated conjunct polymers are soluble for a time sufficient to hydrogenate at least a portion of the conjunct polymers; and recovering the saturated conjunct polymers.
8. The process of claim 7, wherein the saturated conjunct polymers are a clear and colorless oil.
9. The process of claim 7, wherein the hydrogenation component comprises palladium, platinum, or ruthenium.
10. The process of claim 9, wherein the hydrogenation component comprises palladium.
11. The process of claim 7, wherein the conjunct polymer is recovered by solvent extraction.
12. The process of claim 7, wherein the hydrogenation conditions include temperatures of −20° C. to 200° C.
13. The process of claim 7, wherein the supported hydrogenation catalyst is supported on carbon.
14. A process for regenerating a used acidic ionic liquid catalyst, comprising:
    a. contacting the used acidic ionic liquid catalyst and hydrogen with a hydrogenation catalyst comprising a hydrogenation component under hydrogenation conditions; and
    b. recovering a conjunct polymer that is a clear and colorless oil from the used acidic ionic liquid catalyst.
15. The process of claim 14, wherein the hydrogenation component comprises palladium, platinum, or ruthenium.
16. The process of claim 15, wherein the hydrogenation component comprises palladium.
17. The process of claim 14, wherein the conjunct polymer is recovered by solvent extraction.
18. The process of claim 14, wherein the hydrogenation conditions include temperatures of −20° C. to 200° C.
19. The process of claim 14, wherein the hydrogenation catalyst is supported on carbon.
20. The process of claim 14, wherein the used acidic ionic liquid catalyst has increased activity for paraffin alkylation after the contacting step.

* * * * *